United States Patent
Zhang et al.

(10) Patent No.: US 7,026,304 B2
(45) Date of Patent: Apr. 11, 2006

(54) 2-ALKYLATED-CYCLODEXTRIN DERIVATIVES: REVERSAL AGENTS FOR DRUG-INDUCED NEUROMUSCULAR BLOCK

(75) Inventors: Mingqiang Zhang, Newhouse (GB); Gary Tarver, Newhouse (GB)

(73) Assignee: Akzo Nobel N.V., Arnham (NL)

( * ) Notice: Subject to any disclaimer, the term of this patent is extended or adjusted under 35 U.S.C. 154(b) by 224 days.

(21) Appl. No.: 10/468,072

(22) PCT Filed: Feb. 14, 2002

(86) PCT No.: PCT/EP02/01667

§ 371 (c)(1),
(2), (4) Date: Dec. 8, 2003

(87) PCT Pub. No.: WO02/064635

PCT Pub. Date: Aug. 22, 2002

(65) Prior Publication Data

US 2004/0106575 A1    Jun. 3, 2004

(30) Foreign Application Priority Data

Feb. 14, 2001 (EP) .................................. 01200535

(51) Int. Cl.
*A61K 31/715* (2006.01)

(52) U.S. Cl. .......................................... 514/58; 549/14
(58) Field of Classification Search .................. 514/58; 549/14

See application file for complete search history.

(56) References Cited

FOREIGN PATENT DOCUMENTS

JP        11246603        9/1999

OTHER PUBLICATIONS

Lindberg B et al: "Synthesis of some 2-0-(2-Hydroxyalkyl) and 2-0-(2,3-DI-HYDROXYALKYL) Derivatives of Cyclomaltoheptaose"; Carbohydrate Research, NL, Elsevier Scientific Publishing Company. Amsterdam, vol. 222, No. 1, Dec. 30, 1991, pp. 113-119.

Khan A R et al: "Methods for Selective Modifications of Cyclodextrins"; Chemical Reviews, US, American Chemical Society. Easton, vol. 98, No. 5, Jul. 1, 1998, pp. 1977-1996.

*Primary Examiner*—James O. Wilson
*Assistant Examiner*—Jason H. Johnsen
(74) *Attorney, Agent, or Firm*—Mark W. Milstead; F. Aaron Dubberley

(57) ABSTRACT

Disclosed are 2-alkylated-cyclodextrin derivatives and pharmaceutically acceptable salts thereof. The 2-alkylated-cyclodextrin derivatives are suitable for use in the reversal of drug-induced neuromuscular block.

8 Claims, No Drawings

2-ALKYLATED-CYCLODEXTRIN DERIVATIVES: REVERSAL AGENTS FOR DRUG-INDUCED NEUROMUSCULAR BLOCK

This application is the National Stage of International Application No. PCT/EP02/01667, filed Feb. 14, 2002.

The invention relates to 2-alkylated-cyclodextrin derivatives, to their use for the preparation of a medicament for the reversal of drug-induced neuromuscular block, and to a kit for providing neuromuscular block and its reversal.

A neuromuscular blocking agent (NMBA, also called a muscle relaxant) is routinely used during the administration of anaesthesia to facilitate endotracheal intubation and to allow surgical access to body cavities, in particular the abdomen and thorax, without hindrance from voluntary or reflex muscle movement. NMBAs are also used in the care of critically-ill patients undergoing intensive therapy, to facilitate compliance with mechanical ventilation when sedation and analgesia alone have proved inadequate, and to prevent the violent muscle movements that are associated with electroconvulsive therapy treatment.

Based on their mechanisms of action, NMBAs are divided into two categories: depolarizing and non-depolarizing. Depolarizing neuromuscular blocking agents bind to nicotinic acetylcholine receptors (nAChRs) at the neuromuscular junction in a way similar to that of the endogenous neurotransmitter acetylcholine. They stimulate an initial opening of the ion channel, producing contractions known as fasciculations. However, since these drugs are broken down only relatively slowly by cholinesterase enzymes, compared to the very rapid hydrolysis of acetylcholine by acetylcholinesterases, they bind for a much longer period than acetylcholine, causing persistent depolarization of the end-plate and hence a neuromuscular block. Succinylcholine (suxamethonium) is the best known example of a depolarizing NMBA.

Non-depolarizing neuromuscular blocking agents compete with acetylcholine for binding to muscle nAChRs, but unlike depolarizing NMBAs, they do not activate the channel. They block the activation of the channel by acetylcholine and hence prevent cell membrane depolarization, and as a result, the muscle will become flaccid. Most of the clinically-used NMBAs belong to the non-depolarizing category. These include tubocurarine, atracurium, (cis)atracurium, mivacurium, pancuronium, vecuronium, rocuronium and rapacuronium (Org 9487).

At the end of surgery or a period of intensive care, a reversal agent of NMBAs is often given to the patient to assist the recovery of muscle function. Most commonly used reversal agents are inhibitors of acetylcholinesterase (AChE), such as neostigmine, edrophonium and pyridostigmine. Because the mechanism of action of these drugs is to increase the level of acetylcholine at the neuromuscular junction by inhibiting the breakdown of acetylcholine, they are not suitable for reversal of depolarizing NMBAs such as succinylcholine. The use of AChE inhibitors as reversal agents leads to problems with selectivity, since neurotransmission to all synapses (both somatic and autonomic) involving the neurotransmitter acetylcholine is potentiated by these agents. This non-selectivity may lead to many side-effects due to the non-selective activation of muscarinic and nicotinic acetylcholine receptors, including bradycardia, hypotension, increased salivation, nausea, vomiting, abdominal cramps, diarrhoea and bronchoconstriction. Therefore in practice, these agents can be used only after or together with the administration of atropine (or glycopyrrolate) to antagonize the muscarinic effects of acetylcholine at the muscarinic receptors in the autonomic parasympathetic neuroeffector junctions (e.g. the heart). The use of a muscarinic acetylcholine receptor (mAChR) antagonist such as atropine causes a number of side-effects, e.g., tachycardia, dry mouth, blurred vision, difficulties in emptying the bladder and furthermore may affect cardiac conduction.

A further problem with anticholinesterase agents is that residual neuromuscular activity must be present (>10% twitch activity) to allow the rapid recovery of neuromuscular function. Occasionally, either due to hypersensitivity of the patient or accidental overdose, administration of NMBAs can cause complete and prolonged block of neuromuscular function ("profound block"). At present, there is no reliable treatment to reverse such a 'profound block'. Attempts to overcome a 'profound block' with high doses of AChE inhibitors has the risk of inducing a "cholinergic crisis", resulting in a broad range of symptoms related to enhanced stimulation of nicotinic and muscarinic receptors.

In the International Application WO 01/12202 (AKZO Nobel N.V.) the use of chemical chelators (or sequestrants) as reversal agents has been disclosed. Chemical chelators capable of forming a guest-host complex for the manufacture of a medicament for the reversal of drug-induced neuromuscular block were described. The use of chemical chelators as reversal agents for NMBAs has the advantage that they are effective in reversing the action of both depolarizing and non-depolarizing NMBAs. Their use does not increase the level of acetylcholine and therefore they produce fewer side effects and none associated with the stimulation of muscarinic and nicotinic receptors seen with the AChE reversal agents. In addition, there is no need for the combined use of an AChE inhibitor and a mAChR antagonist (e.g., atropine), while the chemical chelators may further be safely employed for the reversal of 'profound block'. Examples of such chemical chelators, as disclosed in WO 01/12202, were selected from various classes of, mostly cyclic, organic compounds which are known for their ability to form inclusion complexes with various organic compounds in aqueous solution, e.g. cyclic oligosaccharides, cyclophanes, cyclic peptides, calixarenes, crown ethers and aza crown ethers.

The cyclodextrins,

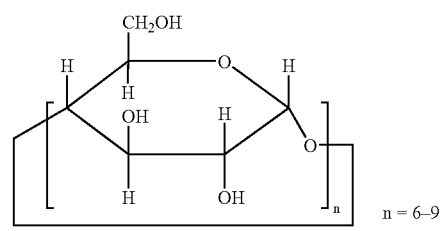

a class of cyclic molecules containing six or more α-D-glucopyranose units linked at the 1,4 positions by α-linkages as in amylose, and derivatives thereof, were identified in WO 01/12202 as particularly useful in the reversal of many of the commonly used neuromuscular blocking agents, or muscle relaxants, such as rocuronium, pancuronium, vecuronium, rapacuronium, mivacurium, atracurium, (cis)atracurium, succinylcholine and tubocurarine.

It has now been found that 2-alkylated-cyclodextrin derivatives having the general formula I

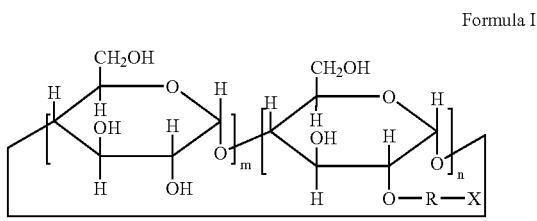

Formula I wherein m is 0–7 and n is 1–8 and m+n=7 or 8;
R is $(CH_2)_p$-phenylene-$(CH_2)_q$, $(C_{1-6})$alkylene, or $(CH_2)_r$—S—$(C_{1-4})$alkylene, of which each alkylene group may be substituted with 1–3 OH groups;
p and r are independently 1–4;
q is 0–4;
X is COOH, $SO_2OH$, $(CH_2$—$CH_2$—$O)_s$—H or OH;
s is 1–3;
or a pharmaceutically acceptable salt thereof;
are highly active in vivo in the reversal of the action of neuromuscular blocking agents.

The term phenylene as used in the definition of formula I means a bivalent radical from benzene the free valencies of which can be positioned either ortho (1,2-phenylene), meta (1,3-phenylene) or para (1,4-phenylene) to one another.

The term $(C_{1-6})$alkylene means a branched or straight chain bivalent carbon radical containing 1–6 carbon atoms, such as methylene, ethylene (1,2-ethandiyl), propylene (1-methyl-1,2-ethanediyl), 2-methyl-1,2-ethanediyl, 2,2-dimethyl-1,2-ethanediyl, 1,3-propanediyl, 1,4-butanediyl, 1,5-pentanediyl and 1,6-hexanediyl.

The term $(C_{1-4})$alkylene as used in the definition of formula I means a branched or straight chain bivalent carbon radical containing 1–4 carbon atoms, such as methylene, ethylene (1,2-ethandiyl), propylene (1-methyl-1,2-ethanediyl), 2-methyl-1,2-ethanediyl, 2,2-dimethyl-1,2-ethanediyl and 1,3-propanediyl.

Compounds according to formula I wherein n+m is 7 are derivatives of β-cyclodextrin, those wherein n+m is 8 are derived from γ-cyclodextrin.

Preferred are the 2-alkylated-cyclodextrin derivatives of formula I wherein X is COOH, or a pharmaceutically acceptable salt thereof.

More preferred are the 2-alkylated-γ-cyclodextrin derivatives of formula I wherein n is 8, R is $(CH_2)_p$-phenylene-$(CH_2)_q$, p is 1, q is 0 and X is COOH.

In the context of the present invention the term drug-induced neuromuscular block refers to the action of clinically-used neuromuscular blocking agents.

No protection per se is sought for the compounds according to formula I wherein m+n=7, n is 1, X is OH and R is 2-methyl-1,2-ethanediyl, 2,2-dimethyl-1,2-ethanediyl, 2-hydroxy-1,3-propanediyl or 2-hydroxy-2-methyl-1,3-propanediyl. These β-cyclodextrin derivatives according to Formula I are described by Lindberg, B. et al (*Carbohydrate Research* 1991, 222, 113–119) in a synthetic study without mentioning any pharmacological activity.

The 2-alkylated-cyclodextrin derivatives of formula I can be prepared by using methods know in the art of selective modifications of cyclodextrins, for example by methods described by Khan et al. (Chem. Rev. 1998, 98, 1977–1996).

In a general method for the preparation of the 2-alkylated β- an γ-cyclodextrin derivatives of formula I, cyclodextrin derivatives of which the 6-positions are protected by a suitable protecting group, such as a silyl group, preferably the tert-butyldimethylsilyl (TBDMS) group, are treated with a strong base, like barium hydroxide or sodium hydride, to selectively generate the 2-alkoxide derivative, which is then reacted with a compound of structure.

X'—R-Hal, wherein R has the meaning as previously defined, Hal means halogen, like iodo, bromo or chloro, X' represents a functional group X (COOH, $SO_2OH$, $(CH_2$—$CH_2$—$O)_s$—H or OH), which has been protected by a suitable protecting group, preferably a silyl based protecting group such as the TBDMS group, the trimethylsilyl or 2-(trimethylsilyl)ethyl group, after which the protecting groups are removed.

In a more specific method for the preparation of the 2-alkylated cyclodextrin derivatives of formula I, use is made of the O-2→O-3 migration of silyl-groups, especially of the tert-butyldimethylsilyl (TBDMS), during the alkylation of 2,6-di-TBDMS-γ- and -β-cyclodextrins, as described by Ashton et al. (J. Org. Chem. 1995, 60, 3898–3903) and Icheln et al. (Carbohydrate Research 1996, 280, 237–250).

Accordingly, 2-alkylated-cyclodextrin derivatives of formula I can be prepared as depicted in scheme I, by conversion of β-cyclodextrin (formula II; x=7) or of γ-cyclodextrin (formula II; x=8) to the known 2,6-di-O-TBDMS-cyclodextrins of formula III (step i), which are alkylated in the presence of a strong base, like sodium hydride, with a compound of structure X'—R-Hal (step ii), wherein X', R and Hal have the meaning as previously defined, followed by removal of protecting groups (step iii).

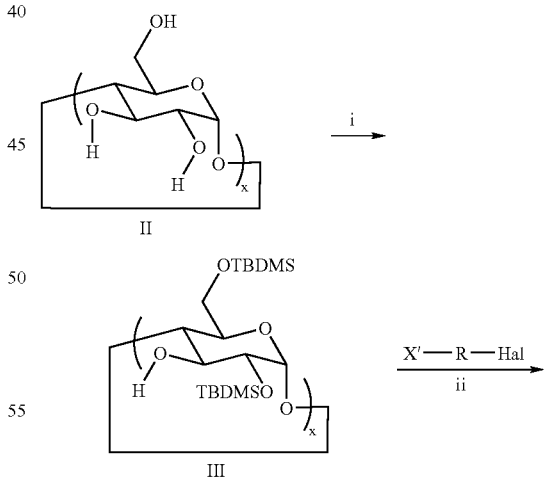

Scheme I

-continued

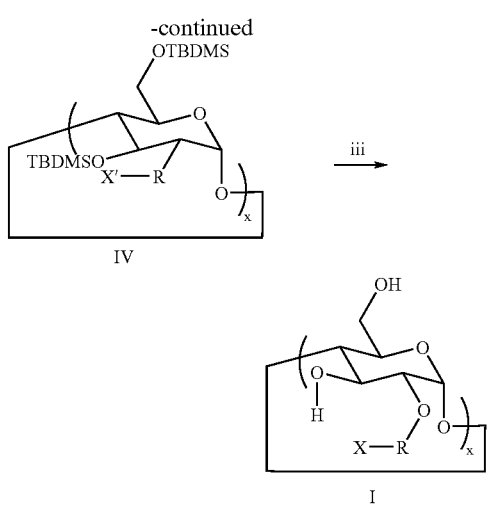

Alternative synthesis routes for the preparation of the 2-alkylated-cyclodextrin derivatives of the invention are known to the skilled person. The chemistry of the derivatisation of cyclodextrins is well documented (see for example: *Comprehensive Supramolecular Chemistry*, Volumes 1–11, Atwood J. L., Davies J. E. D., MacNicol D. D., Vogtle F., eds; Elsevier Science Ltd., Oxford, UK, 1996).

Pharmaceutically acceptable salts of 2-alkylated-cyclodextrin derivatives of formula I wherein X represents the carboxylic acid group COOH or the sulphonic acid group $SO_2OH$, may be obtained by treating the acid with an organic base or a mineral base, like sodium-, potassium- or lithium hydroxide.

The 2-alkylated-cyclodextrin derivatives, or pharmaceutically acceptable salts or solvates thereof, for use in the invention are administered parenterally. The injection route can be intravenous, subcutaneous, intradermal, intramuscular, or intra-arterial. The intravenous route is the preferred one. The exact dose to be used will necessarily be dependent upon the needs of the individual subject to whom the medicament is being administered, the degree of muscular activity to be restored and the judgement of the anaesthetist/critical-care specialist. Extracorporal application of the chemical chelators of the invention, for instance by mixing of the chemical chelator with the blood during dialysis or during plasmaphoresis, is also contemplated.

In a further aspect the invention relates to a kit for providing neuromuscular block and its reversal comprising (a) a neuromuscular blocking agent, and (b) a 2-alkylated-cyclodextrin derivative according to general formula I capable of forming a guest-host complex with the neuromuscular blocking agent. With a kit according to the invention is meant a formulation, which contains separate pharmaceutical preparations, i.e. the neuromuscular blocking agent and a 2-alkylated-cyclodextrin derivative of formula I, i.e. the reversal agent. The components of such a kit of parts are to be used sequentially, i.e. the neuromuscular blocking agent is administered to a subject in need thereof, which is followed, at a point in time when restoration of muscle function is required, by the administration of the reversal agent, i.e. a 2-alkylated-cyclodextrin derivative of the present invention.

A preferred kit, according to the invention, contains a 2-alkylated-cyclodextrin derivative of formula I and an aminosteroidal neuromuscular blocking agent. The 2-alkylated-cyclodextrin derivatives of the invention are especially suitable for the reversal of neuromuscular block induced by the aminosteroidal neuromuscular blocking agents rocuronium, vecuronium, pancuronium and rapacuronium. A particularly preferred kit of the invention comprises rocuronium as the neuromuscular blocking agent.

Mixed with pharmaceutically suitable auxiliaries and pharmaceutically suitable liquids, e.g. as described in the standard reference, Gennaro et al., Remington's Pharmaceutical Sciences, (18th ed., Mack Publishing Company, 1990, Part 8: Pharmaceutical Preparations and Their Manufacture; see especially Chapter 84 on "Parenteral preparations", pp. 1545–1569; and Chapter 85 on "Intravenous admixtures", pp. 1570–1580) the 2-alkylated-cyclodextrin derivatives can be applied in the form of a solution, e.g. for use as an injection preparation.

Alternatively, the pharmaceutical composition may be presented in unit-dose or multi-dose containers, for example sealed vials and ampoules, and may be stored in a freeze dried (lyophilised) condition requiring only the addition of the sterile liquid carrier, for example, water prior to use.

The invention further includes a pharmaceutical formulation, as hereinbefore described, in combination with packaging material suitable for said composition, said packaging material including instructions for the use of the composition for the use as hereinbefore described.

The invention is illustrated in the following examples:

EXAMPLE 1

General Synthesis of
per-2-O-(alkylated)-cyclodextrins

To a solution of heptakis-per-6-O-(tert-butyldimethylsilyl)-β-cyclodextrin (0.5 g, 0.25 mmol) or octakis-per-6-O-(tert-butyldimethylsilyl)-γ-cyclodextrin (0.5 g, 0.225 mmol) in dimethylformamide (20 ml) was added barium hydroxide octahydrate (0.5 g, 1.58 mmol) followed by barium oxide (0.9 g, 5.87 mmol). The desired alkylating agent (2 equivalents per secondary hydroxyl) was added and the reaction stirred for 24 hours. The reaction mixture was filtered to remove barium oxide and poured into water to remove barium hydroxide. The crude cyclodextrin precipitate was dissolved in dichloromethane and dried (sodium sulfate). The solution was filtered and the solvent evaporated to a small volume. Methanol was added to triturate the compound which was then filtered and dried in vacuo.

EXAMPLE 2

Octakis per-2-O-(3-carboxybenzyl)-γ-cyclodextrin,
Na salt

A: 2-(trimethylsilyl)ethyl-3-(iodomethyl)benzoate

To a solution of 3-(chloromethyl)benzoyl chloride (2.5 g, 17.5 mmol) in dichloromethane (100 ml) was added 2-(trimethylsilyl)ethanol (1.72 ml, 12.0 mmol). Triethylamine, (9.21 ml, 66 mmol) was added and the reaction stirred overnight. The dichloromethane was evaporated and the crude material taken up in ether and washed with water. The ether layer was dried (sodium sulfate) and evaporated to give a slightly yellow mobile oil. The oil (2.7 g) was dissolved in acetone (30 ml) containing sodium iodide (1.5 g) and stirred for two hours. The solvent was removed and to the residue was added diethyl ether and the resulting mixture was filtered. The filtrate was evaporated to give a brown oil (3.68 g, 77%): $^1$H NMR (CDCl$_3$) δ: 7.95, (1H, s), 7.85, (1H, d), 7.28, (1H, d), 7.17, (1H, t), 4.38, (2H, s), 4.33 (2H, m), 1.11 (2H, m), 0.00 (9H, s) ppm. Mass spectrum (M-I) 235.

B: Octakis per-2-O-[3-{2-(trimethylsilyl) ethylcarboxy}benzyl]-per-6-O-(tert-butyl-dimethyl-silyl)-γ-cyclodextrin Using the general procedure described in Example 1, the title compound was obtained from the reaction of octakis-per-6-O-(tert-butyldimethylsilyl)-γ-cyclodextrin with the alkylating agent described under A.

C: Octakis per-2-O-(3-carboxybenzyl)-γ-cyclodextrin sodium salt

Tetrabutyl ammonium fluoride (TBAF; 17.65 ml, 1.0 M solution in tetrahydrofuran, 17.6 mmole) was added to a solution of per-2-O-[3-{2-(trimethylsilyl) ethylcarboxy}benzyl]-per-6-O-(tert-butyldimethylsilyl)-γ-cyclodextrin (2.4 g, 0.59 mmol) in tetrahydrofuran (30 ml). The reaction mixture was refluxed for 2 h and allowed to cool to room temperature. The solvent was removed under reduced pressure and to the residue was added water (150 ml). The pH was adjusted to 4 by addition of 2M hydrochloric acid and the solid formed was filtered off. Washing with acetone gave 1.2 g of per-2-O-(3-carboxybenzyl)-γ-cyclodextrin as a pale solid. To this was added methanol (100 ml) and sodium hydroxide (0.16 g, 4.1 mmoles) and the suspension was stirred until dissolution had occurred. The solvent was removed under reduced pressure and water was added (30 ml). This solution was dialysed against several changes of water. The resulting solution was evaporated under reduced pressure to give a gum. Stirring with acetone gave a solid which was filtered to give the title compound as a tan solid (1.1 g, 73%). Electrospray MS (M+Na)$^+$ 2393.1; $^1$H NMR (D$_2$O); δ 3.47 (t, 8H), 3.54–3.57 (m, 8H), 3.67–3.74 (m, 24H), 3.86 (t, 8H), 4.70–4.75 (m, 8H), 4.84 (d, 8H), 5.07 (d, 8H), 7.50 (t, 8H), 7.56 (d, 8H), 7.88–7.90 (m, 16H) ppm.

EXAMPLE 3

Octakis per-2-O-(4-carboxybenzyl)-γ-cyclodextrin, Na salt

A: 2-(trimethylsily)ethyl-4-(iodomethyl)benzoate

To a solution of 4-(chloromethyl)benzoyl chloride (2.5 g, 13.22 mmol) in dichloromethane (100 ml) was added 2-(trimethylsilyl)ethanol (1.72 ml, 12.0 mmol). Triethylamine (9.21 ml, 66 mmol) was added and the reaction mixture stirred overnight. The dichloromethane was evaporated and the crude material taken up in ether and washed with water. The ether layer was dried (sodium sulfate) and evaporated to give a slightly yellow mobile oil. The oil (2.7 g) was dissolved in acetone (30 ml) containing sodium iodide (1.5 g) and stirred for two hours. The solvent was removed, ether added and the reaction filtered. The filtrate was then evaporated to give the title compound as a brown temperature unstable oil, 3.58 g, 75%.

$^1$H NMR (CDCl$_3$) δ: 7.88 (2H, d), 7.34 (2H, d), 4.38 (2H, s), 4.32 (2H, m), 1.04 (2H, m), 0.01 (9H, s) ppm. Mass spectrum (M-I) 235

B: Octakis per-2-O-[4-{2-(trimethylsilyl) ethylcarboxy}benzyl]-per-6-O-(tert-butyldimethylsilyl)-γ-cyclodextrin Using the general procedure described in Example 1, the title compound was obtained from the reaction of octakis-per-6-O-(tert-butyldimethylsilyl)-γ-cyclodextrin with the alkylating agents described under A.

C: Octakis per-2-O-(4-carboxybenzyl)-γ-cyclodextrin, Na salt

Using the methodology described in example 2C, per-2-O-[4-{2-(trimethylsilyl)ethylcarboxy}benzyl]-per-6-O-(tert-butyldimethylsilyl)-γ-cyclodextrin was deprotected and converted to the sodium salt to give the title compound.

Electrospray Mass Spectrum M+ 2545.2. $^1$H NMR (CDCl$_3$) δ: 7.9 (2H), 7.5 (2H), 5.1 (1H), 4.9 (2H), 4.7–3.95 (1H), 3.7 (3H), 3.55 (2H) ppm.

EXAMPLE 4

Octakis per-2-O-(2-carboxybenzyl)-γ-cyclodextrin, Na salt

Octakis per-6-O-TBDMS-γ-cyclodextrin (15 g) was dissolved in tetrahydrofuran (THF; 300 ml) and sodium hydride (2.72 g, 60% in oil) was added portionwise. Ethyl-2-iodomethyl benzoate (25.6 g) in THF (100 ml) was slowly added and the reaction mixture was stirred for 4 days. The reaction mixture was concentrated and purified by column chromatography on silica gel using stepwise elution with dichloromethane/ethyl acetate 20:1, 10:1 to 5:1. The pure fractions were combined and evaporated to give the ethyl ester product (3.8 g) as a foam. This was dissolved in THF (60 ml) and to the solution was added tetrabutylammonium fluoride (17.35 ml, 1.0 M in THF). The mixture was refluxed for 4 hours and then concentrated under vacuum. Water was then added to form a gum. The water was decanted, acetone added and the compound precipitated as a brown solid. The solid was dissolved in methanol (70 ml) and sodium hydroxide solution added (5 g in water (50 ml)). The mixture was stirred for 24 hr and the methanol evaporated. The crude solution was dialysed in 1000 MWCO tubing followed by evaporation and precipitation with acetone. Excess TBAF salts were removed by stirring overnight in water with Dowex® 50W-X8 resin, followed by evaporation and stirring with acetone. Drying gave the product (1.6 g) as a tan solid. $^1$H NMR (D$_2$O) δ: 7.7–8.1 (4H), 5.4 (1H), 4.9 (2H), 3.9–4.7 (6H) ppm. Electrospray Mass Spectrum m/z M-H 2367.4

EXAMPLE 5

Mono-2-O-(4-carboxybenzyl)-γ-cyclodextrin sodium salt

To dried γ-CD (15 g) in dimethylformamide (400 ml) was added sodium hydride (464 mg, 60% in oil). To the mixture, a solution of methyl-4-iodomethyl benzoate (3.19 g) in dimethylformamide (100 ml) was slowly added. The reaction mixture was left to stir for 2 days. The solvents were removed and the reaction triturated with acetone to give the methyl ester (19.97 g) as a white solid. This white solid of mono-2-O-(4-methoxycarbonyl)-γ-cyclodextrin (5 g) was dissolved in water (60 ml) containing sodium hydroxide (138 mg). The reaction mixture was stirred for 24 hr, evaporated and the sodium salt purified on Sephadex® DEAE resin eluting with 0.1 M NaOH to give 5.28 g of a white solid. Dialysis in 1000 MWCO tubing followed by evaporation gave the mono substituted compound (700 mg).
$^1$H NMR (D$_2$O) δ: 7.91 (m), 7.54 (m), 5.11 (m), 5.09, 4.1–3.5 (m) ppm. Electrospray MS m/z M-H—Na 1429

EXAMPLE 6–10

General Synthesis of 2-(4-thia-alkyl)cyclodextrins

2-Alkylated-cyclodextrin derivatives which contain a sulfur atom at the 4-position of the side chain, i.e. compounds of general formula I wherein R is (CH$_2$)$_r$—S—(C$_{1-4}$)alkylene and r is 3, were prepared by radical addition of an appropriate thiol to per-2-allyl-β-cyclodextrin or to per-2-allyl-γ-cyclodextrin, which were prepared as described by Icheln et al (Carbohydrate Research 280, 1996, 237–250).

The appropriate 2-allyl-cyclodextrin and thiol (1.5–3 equivalents per allyl group) were dissolved in acetonitrile, water, methanol or toluene or a miscible mixture of the above. The reaction mixture was thoroughly degassed with either nitrogen or argon and then heated at 110° C. for 2–24 h in the presence of catalytic amounts of AIBN (2,2'-azobis (isobutyronitrile); 10–20 mg per 250 mg of CD).

After the desired reaction time the crude reaction mixture was stripped of solvent and an NMR performed to check for remaining allyl functionality. If the reaction was found incomplete, which was usually due to precipitation of reactants in the mixture, the reaction was resubmitted to thiol and AIBN in a solvent system in which complete solubility could be maintained, typically water/methanol. The crude reaction mixture was stripped of solvent and purified of starting thiol by dialysis in water using 1000 MWCO (molecular weight cut-off) dialysis tubing. G25 size exclusion Sephadex was used to removed trace amounts of thiol.

EXAMPLE 6

Octakis per-2-O-(6-carboxy-4-thia-hexyl)-γ-cyclodextrin, Na salt

The title compound was obtained via the addition reaction of 3-mercaptopropionic acid to per-2-allyl-γ-cyclodextrin.
1H NMR (D$_2$O) δ: 5.4 (1H), 4.0 (1H), 3.75–3.95 (1H), 3.65 (3H), 3.45 (1H), 2.77 (1H), 2.68 (1H), 2.48 (1H), 1.9 (1H) ppm. m/z M-2H 1233.

EXAMPLE 7

Octakis per-2-O-(5-carboxy-4-thia-pentyl)-γ-cyclodextrin, Na salt

The title compound was obtained via the addition reaction of 2-mercaptoacetic acid to per-2-allyl-γ-cyclodextrin.
1H NMR (D$_2$O) δ: 5.3 (1H), 3.45 (1H), 4.0 (1H), 3.6 (1H), 3.85 (1H), 3.8–3.85 (2H), 2.7 (1H), 1.95 (1H) ppm. IR v: 3417, 2932, 1587, 1391, 1164, 1037 cm$^{-1}$.

EXAMPLE 8

Octakis per-2-O-(6-sulfo-4-thia-hexyl)-γ-cyclodextrin, Na salt

The title compound was obtained via the addition reaction of 2-sulfoethanethiol to per-2-allyl-γ-cyclodextrin.

$^1$H NMR (D$_2$O) δ: 5.3 (1H), 4.0 (1H), 3.7–3.85 (3H), 3.6 (1H), 3.4 (1H), 3.1 (1H), 2.8–2.85 (1H), 2.65 (1H), 1.9 (1H) ppm.

EXAMPLE 9

Heptakis per-2-O-(6,7-dihydroxy-4-thia-heptyl)-β-cyclodextrin

The title compound was obtained via the addition reaction of 2,3-dihydroxypropanethiol to per-2-allyl-β-cyclodextrin.
$^1$H NMR (D$_2$O) δ: 5.1 (1H), 3.95 (1H), 3.7–3.9 (1H), 3.45 (1H), 3.45 (4H), 3.4 (1H), 3.5–3.6 (1H) 2.5–2.7 (2H), 1.85 (1H) ppm. m/z M-H 2156.

EXAMPLE 10

Heptakis per-2-O-(9-hydroxy-7-oxa-4-thia-nonyl)-β-cyclodextrin

The title compound was obtained via the addition reaction of 5-hydroxy-3-oxapentanethiol to per-2-allyl-β-cyclodextrin.
$^1$H NMR (D$_2$O) δ: 5.15 (1H), 3.85–4.0 (2H), 3.6–3.9 (5H), 3.6–3.9 (1H), 3.4–3.5 (2H), 2.8 (1H), 2.7 (1H), 1.9 (1H) ppm. m/z M-CO$_2$H 2315.

EXAMPLE 11

Reversal of Neuromuscular Blockade in Anaesthetized Guinea Pigs in vivo

Male Dunkin-Hartley guinea pigs (bodyweight: 600–900 g) were anaesthetized by i.p. administration of 10 mg/kg pentobarbitone and 1000 mg/kg urethane. After tracheotomy, the animals were artificially ventilated using a Harvard small animal ventilator. A catheter was placed into the carotid artery for continuous monitoring of arterial blood pressure and the taking of blood samples for blood gas analysis. Heart rate was derived from the blood pressure signal. The sciatic nerve was stimulated (rectangular pulses of 0.5 ms duration at 10 s (0.1 Hz) intervals at a supramaximal voltage, using a Grass S88 Stimulator) and the force of M. gastrocnemius contractions was measured using a Grass FT03 force-displacement transducer. Contractions, blood pressure and heart rate were recorded on a multichannel Grass 7D recorder. Catheters were placed in both jugular veins. One catheter was used for the continuous infusion of a neuromuscular blocking agent. The infusion rate of the neuromuscular blocking agent was increased until a steady-state block of 85–90% was obtained. The other catheter was used for administration of increasing doses of the reversal agent. During continuous infusion of the neuromuscular blocking agent, single doses of increasing concentration of reversal agent were given. At the end of the experiment, the measured force of muscle contractions was plotted against the concentration of reversal agent, and using regression analysis techniques, the 50% reversal concentration was calculated. Results for the reversal of the neuromuscular block, induced by the muscle relaxant rocuronium bromide (Roc), by the 2-alkylated-cyclodextrin derivatives of Examples 2–10 are presented in Table I. For comparison, the reversal activity of the parent compounds β-cyclodextrin and γ-cyclodextrin, as already described in WO 01/12202 (AKZO Nobel N.V.), are included as well.

TABLE I

Dose ($ED_{50}$, µmol · kg$^{-1}$) producing 50% reversal of steady-state neuromuscular block in anaesthetized guinea pigs and concentration at maximum reversal.

| Compound | $ED_{50}$ µmol · kg$^{-1}$ | % max reversal at conc. (µmol · kg$^{-1}$) |
|---|---|---|
| Octakis per-2-O-(4-carboxybenzyl)-γ-cyclodextrin, Na salt (Example 3) | 0.20 | 97 (0.8) |
| Octakis per-2-O-(3-carboxybenzyl)-γ-cyclodextrin, Na salt (Example 2) | 0.38 | 104 (4.8) |
| Octakis per-2-O-(2-carboxybenzyl)-γ-cyclodextrin, Na salt (Example 4) | 3.4 | 84 (15) |
| Mono-2-O-(4-carboxybenzyl)-γ-cyclodextrin, Na salt (Example 5) | 0.25 | 96 (2.6) |
| Octakis per-2-O-(6-carboxy-4-thia-hexyl)-γ-cyclodextrin, Na salt (Example 6) | 3.4 | 86 (16) |
| Octakis per-2-O-(5-carboxy-4-thia-pentyl)-γ-cyclodextrin, Na salt (Example 7) | 1.12 | 91 (10) |
| Octakis per-2-O-(6-sulfo-4-thia-hexyl)-γ-cyclodextrin, Na salt (Example 8) | 1.4 | 85 (4.5) |
| Heptakis per-2-O-(6,7-dihydroxy-4-thia-heptyl)-β-cyclodextrin (Example 9) | 1.10 | 93 (6.4) |
| Heptakis per-2-O-(9-hydroxy-7-oxa-4-thia-nonyl)-β-cyclodextrin (Example 10) | 5.6 | 72 (12) |
| γ-cyclodextrin (γ-CD) | 4 | 104 (47) |
| β-cyclodextrin (β-CD) | 20 | 93 (113) |

We claim:

1. A 2-alkylated-cyclodextrin derivative represented by formula I

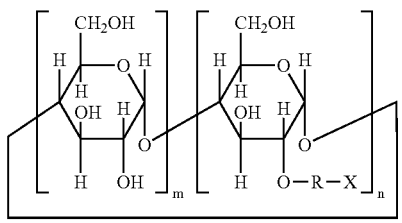

Formula I wherein m is 0–7 and n is 1–8 and m+n=7 or 8;
R is $(CH_2)_p$-phenylene-$(CH_2)_q$, $(C_{1-6})$alkylene, or $(CH_2)_r$—S—$(C_{1-4})$alkylene, of which each alkylene group may be substituted with 1–3 OH groups;
p and r are independently 1–4;
q is 0–4;
X is COOH, SO$_2$OH, $(CH_2$—$CH_2$—O)$_s$—H or OH;
s is 1–3; or
a pharmaceutically acceptable salt thereof; with the proviso that when m+n=7, n is 1 and X is OH, R cannot be 2-methyl-1,2-ethanediyl, 2,2-dimethyl-1,2-ethanediyl, 2-hydroxy-1,3-propanediyl or 2-hydroxy-2-methyl-1,3-propanediyl.

2. The 2-alkylated-cyclodextrin derivative according to claim 1, wherein X is COOH.

3. The 2-alkylated-cyclodextrin derivative according to claim 1, wherein X is COOH; m is 0; n is 8; and R is $(CH_2)_p$-phenylene-$(CH_2)_q$; p is 1 and q is 0.

4. A kit for providing neuromuscular block and its reversal, comprising:
   (a) neuromuscular blocking agent, and
   (b) a 2-alkylated-cyclodextrin derivative according to claim 1.

5. The kit according to claim 4, wherein the neuromuscular blocking agent is selected from the group consisting of rocuronium, vecuronium, pancuronium and rapacuronium.

6. The kit according to claim 5, wherein the neuromuscular blocking agent is rocuronium.

7. A method for reversal of drug-induced neuromuscular block in a patient, comprising: parenterally administering to said patient in need thereof an effective amount of a 2-alkylated-cyclodextrin derivative according to claim 1.

8. A pharmaceutical composition, comprising:
a 2-alkylated-cyclodextrin derivative represented by general formula I

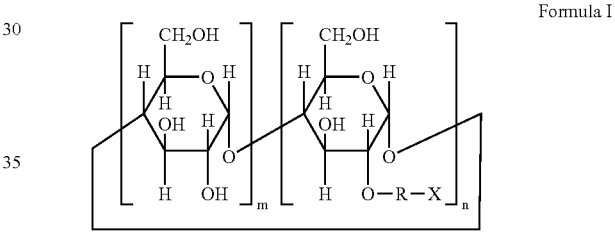

Formula I wherein m is 0–7 and n is 1–8 and m+n=7 or 8;
R is $(CH_2)_p$-phenylene-$(CH_2)_q$, $(C_{1-6})$alkylene, or $(CH_2)_r$—S—$(C_{1-4})$alkylene, of which each alkylene group may be substituted with 1–3 OH groups;
p and r are independently 1–4;
q is 0–4;
X is COOH, SO$_2$OH, $(CH_2$—$CH_2$—O)$_s$—H or OH;
s is 1–3; or
a pharmaceutically acceptable salt thereof, and pharmaceutically acceptable auxilliaries.

* * * * *

UNITED STATES PATENT AND TRADEMARK OFFICE
CERTIFICATE OF CORRECTION

PATENT NO. : 7,026,304 B2
APPLICATION NO. : 10/468072
DATED : April 11, 2006
INVENTOR(S) : Zhang et al.

It is certified that error appears in the above-identified patent and that said Letters Patent is hereby corrected as shown below:

Col. 12, Claim 8, Lines 24-25    by "gen-eral formula I"

should read    -- by formula I --

Col. 12, Claim 8, Line 50,    "auxilliaries"

should read    -- auxiliaries --

Signed and Sealed this

Twenty-second Day of August, 2006

JON W. DUDAS
*Director of the United States Patent and Trademark Office*